United States Patent [19]

Sasaki

[11] Patent Number: 4,701,739
[45] Date of Patent: Oct. 20, 1987

[54] EXHAUST GAS SENSOR AND PROCESS FOR PRODUCING SAME

[75] Inventor: Kazuko Sasaki, Minoo, Japan

[73] Assignee: Figaro Engineering Inc., Osaka, Japan

[21] Appl. No.: 711,154

[22] Filed: Mar. 13, 1985

[30] Foreign Application Priority Data

Mar. 30, 1984 [JP] Japan ............................ 59-63900
Mar. 30, 1984 [JP] Japan ............................ 59-63901

[51] Int. Cl.$^4$ .............................................. H01L 7/00
[52] U.S. Cl. .................................... 338/34; 422/98; 29/592 R
[58] Field of Search ............... 338/34; 73/23, 27 R; 219/497, 499; 252/518; 29/592 R, 595, 610 R; 204/424, 425; 422/94

[56] References Cited

U.S. PATENT DOCUMENTS

| | | | |
|---|---|---|---|
| 3,946,198 | 3/1976 | Foote | 219/499 X |
| 4,194,994 | 3/1980 | Baresel et al. | 252/518 |
| 4,314,996 | 2/1982 | Serido et al. | 338/34 X |
| 4,459,577 | 7/1984 | Murakami et al. | 338/34 |
| 4,507,643 | 3/1985 | Sunono et al. | 338/34 |

OTHER PUBLICATIONS

Proceedings of the International Meeting on Chemical Sensors, pp. 187–192 (Kodansha, 1983).

Primary Examiner—Clifford C. Shaw
Assistant Examiner—M. M. Lateef
Attorney, Agent, or Firm—Kane, Dalsimer, Kane, Sullivan and Kurucz

[57] ABSTRACT

An exhaust gas sensor including a compound $ASnO_{3-\delta}$ wherein A is Ba, Ra, Sr or Ca to make use of the variation of resistance value of the compound. $BaSnO_{3-\delta}$ and $RaSnO_{3-\delta}$ are n-type semiconductors, while $SrSnO_{3-\delta}$ and $CaSnO_{3-\delta}$ exhibit the behavior of n-type semiconductors at the point of equivalence and the behavior of p-type semiconductors in the lean burn region. The compound $ASnO_{3-\delta}$ is prepared by reacting an alkaline earth with $SnO_2$.

13 Claims, 12 Drawing Figures (No. A42)

2θ(degree)

No. A42 (X10000)

EXHAUST GAS SENSOR AND PROCESS FOR PRODUCING SAME

BACKGROUND OF THE INVENTION

1. Field of the Invention

The present invention relates to an exhaust gas sensor wherein use is made of the variation of resistance of a metallic oxide semiconductor and to a process for producing the same, and more particularly to improvements in exhaust sensor materials.

Exhaust gas sensors are used for detecting the air/fuel ratio λ of exhaust gases or $O_2$, CO or like component of exhaust gases. They are chiefly used for controlling the air/fuel ratio for motor vehicle engines, boilers, etc. and for preventing incomplete combustion in air heaters. For use with motor vehicle engines and boilers, the sensor controls the air/fuel ratio: at the point of equivalence (where the air/fuel ratio λ is 1.00) or in the lean burn region (in which the air/fuel ratio is not smaller than 1). For use in air heaters, the sensor detects the reduction of the air/fuel ratio λ to below 1 and detects incomplete combustion.

BRIEF DESCRIPTION OF THE PRIOR ART

Exhaust gas sensors are known in which a gas sensitive member made of $SnO_2$ is connected to at least one pair of electrodes (as disclosed, for example, in U.S. Pat. No. 4,459,577, corresponding to German Patent Application No. 3,313,752). With the exhaust gas sensor of the patent, the growth of crystals of $SnO_2$ is controlled to give the sensor improved durability against reducing atmospheres of high temperatures.

However, there is a limitation to the improvement of durability by controlling the growth of crystals. Under very severe conditions, for example, when brought into contact with an atmosphere having a temperature of 900° C. and λ of 0.83, $SnO_2$ is reduced and inevitably exhibits a lower resistance value. Another problem of $SnO_2$ is that the compound has higher sensitivity to combustible gases, such as CO and HC, than to $O_2$ and therefore gives a detection result which is shifted toward the rich side (region of λ<1) owing to the presence of remaining unreacted combustible gases. To detect the air/fuel ratio λ with improved precision, there is a need to assure a balance between the sensitivity to combustible gases and sensitivity to oxygen. Another problem of $SnO_2$ is that it is slow in response to the air/fuel ratio. The exhaust gas sensor, which is used chiefly for controlling motor vehicle engines, must have high responsiveness as already known.

Other known literature relating to $SnO_2$ includes U.S. Pat. No. 4,194,994 (corresponding to German Patent Application No. 2,648,373) which discloses that about 0.2 mole % of MgO is added to $SnO_2$ to give the compound improved sensitivity to oxygen.

The literature relating to other exhaust gas sensor materials includes U.S. Pat. No. 3,558,280 (corresponding to British Pat. No. 1,231,140) which discloses an oxygen sensor incorporating a p-type perovskite compound such as $SrFeO_3$. The sensitivity of $SrFeO_3$ to oxygen is shown in British Patent Application No. 8,110,921, and the resistance value thereof decreases in proportion to 1/9th power of oxygen partial pressure. Further the sensitivity of perovskite compounds, such as $LaCoO_3$, to CO or $O_2$ is shown in "Proceedings of the International Meeting on Chemical Sensors," pp. 187–192 (Kodansha, 1983).

SUMMARY OF THE INVENTION

An object of the present invention is to provide a novel exhaust gas sensor material having improved durability to reducing atmospheres of high temperatures and suppressed sensitivity to unburnt combustible gases to prevent the reduction in the precision of detection due to unburnt gases, the sensor material further having improved responsiveness to changes of atmosphere.

Another object of the present invention is to provide a gas sensitive member which is prevented from decomposition due to a solid-phase reaction between the member and alumina when alumina is used as a substrate.

Another object of the present invention is to provide a process for producing exhaust gas sensor materials having the above-mentioned properties.

The present invention provides an exhaust gas sensor which is characterized in that at least one pair of electrodes is connected to a gas sensitive member comprising a compound $ASnO_{3-\delta}$ wherein A is at least one member selected from the group consisting of Ba, Sr, Ca and Ra, and δ is a non-stoichiometric parameter.

Presumably, the compounds $ASnO_{3-\delta}$ are perovskite compounds ("National Bureau of Standards Monograph," Vol. 25, Sec. 3, p. 11, 1964). $BaSnO_{3-\delta}$ and $RaSnO_{3-\delta}$, which are perfectly n-type semiconductors, increase in resistance in response to a change from λ<1 to λ>1 and also to a further increase in λ in the lean burn region. $BaSnO_{3-\delta}$ and $RaSnO_{3-\delta}$ are equivalent to each other and match in characteristics, but it is preferable to use $BaSnO_{3-\delta}$ since $RaSnO_{3-\delta}$ is radioactive. $SrSnO_{3-\delta}$ and $CaSnO_{3-\delta}$ are substances having both n-type properties and p-type properties, exhibit an increased resistance value in response to a change from λ<1 to λ>1 (n-type properties) and decreases in resistance when λ further increases in the lean burn region (p-type properties). The resistance value of these compounds increases in the order of $BaSnO_{3-\delta} < SrSnO_{3-\delta} < CaSnO_{3-\delta}$, and the sensitivity thereof to a change from λ<1 to λ>1 decreases in the order of $BaSnO_{3-\delta} > SrSnO_{3-\delta} > CaSnO_{3-\delta}$. The absolute value of the oxygen sensitivity increases in the order of $BaSnO_{3-\delta} > CaSnO_{3-\delta} = SrSnO_{3-\delta}$. The sensitivity of these compounds increases as the growth of crystals is promoted, such that it increases greatly when the compounds are baked at a temperature of at least 1260° C.

The material for the gas sensitive member is obtained by baking a compound $ASnO_{3-\delta}$ or a substance which is converted to the compound $ASnO_{3-\delta}$ when heated, in a non-reducing atmosphere, preferably at a temperature of 1000° to 2000° C. for 30 minutes to 20 hours.

An exhaust gas sensor is prepared with use of the gas sensitive member, for example, by connecting a pair of electrodes to the gas sensitive member, causing a heat-resistant insulating substrate to support the gas sensitive member and providing a heater around the resulting assembly for heating the member at a specified temperature.

The compound $ASnO_{3-\delta}$ has the property of undergoing a decomposition reaction with alumina which is generally used as the material for the substrate. To prevent the solid-phase reaction, an intermediate layer of a substance which is not reactive with $ASnO_{3-\delta}$ is interposed between the gas sensitive member and the substrate. Examples of preferable materials for the intermediate layer are spinel ($MgAl_2O_4$), mullite ($Al_6Si_2O_{13}$) and cordierite ($Mg_2Al_4Si_5O_{18}$).

BRIEF DESCRIPTION OF THE DRAWINGS

FIG. 4 (B) is a fragmentary enlarged view in section showing the same;

DETAILED DESCRIPTION OF THE PREFERRED EMBODIMENTS

Terminology

Figure 1:
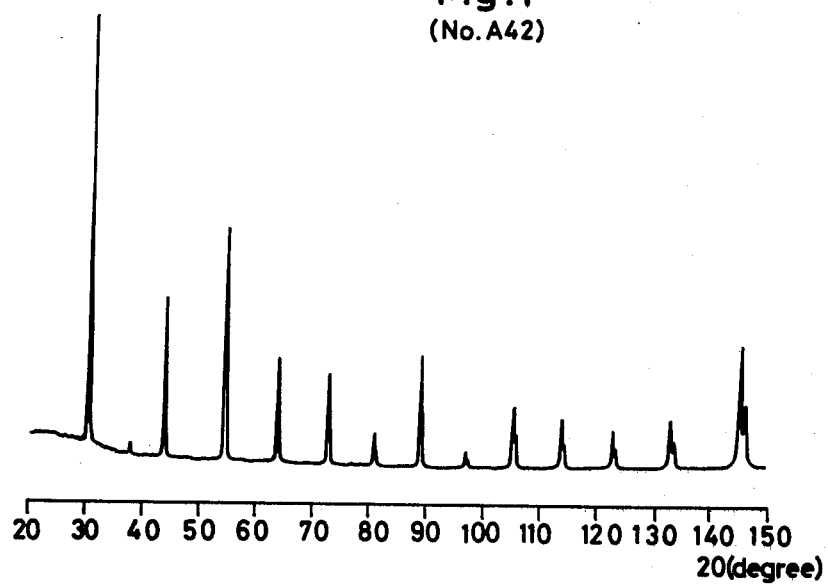
FIG. 1 is an X-ray diffraction diagram of $BaSnO_{3-\delta}$.

In the following description, the compounds $ASnO_{3-\delta}$ will be represented without using the non-stoichiometric parameter $\delta$. The value of this parameter $\delta$, which varies with the ambient atmosphere and temperature, is usually $-0.1$ to $0.5$.

The term "specific surface area" as used herein and in the appended claims refers to a value measured by the B.E.T. method using $N_2$ as the adsorption medium. The term "mean crystallite size" means the average value of crystallite sizes of crystals and is determined by measuring the lengths of the major axis and minor axis of each crystal from an electron photomicrograph and calculating the arithmetic mean of the values. Further oxygen gradient m is included in the concept of oxygen sensitivity. When the resistance value Rs of a sensor is expressed by $Rs = K \cdot P_{O_2}{}^m$ (Equation 1), m is defined as oxygen gradient. It is well known that the resistance of the semiconductor varies according to Equation 1.

Preparation of gas sensitive member

(A) Preparation of $BaSnO_3$ $BaCO_3$ at least 99.99% in purity and $SnO_2$ at least 99.99% in purity (50 m$^2$/g in specific surface area) are kneaded together in an equimolar ratio with use of water. $BaCO_3$ is used as a starting material because it contains a lesser amount of crystal water and adsorbed water, and the amount to be used can be determined with ease. Other Ba materials, such as BaO, $Ba(OH)_2$, $BaCl_2$, $BaSO_4$ and metallic barium, are also usable although difficulty is encountered in controlling the amount to be used. $SnO_2$, which is used similarly because it is easy to control the amount, may be replaced by $SnCl_4$, $SnSO_4$, $Sn(OH)_4$ or the like.

The mixture is then calcined in air at 500° to 1200° C. for 1 hour. Four different temperatures, i.e. 500° C., 800° C., 1000° C. and 1200° C., were used for calcination. When the mixture is calcined at 500° C., the product is a mxiture of $SnO_2$ and $BaCO_3$ and is free from $BaSnO_3$. When heated at 800° C., the starting mixture almost entirely changes to $BaSnO_3$. At a temperature not lower than 1000° C., the mixture is completely converted to $BaSnO_3$. The calcining atmosphere needs only to be non-reducing. An inert atmosphere of 100% $N_2$ or the like, or a strongly oxidizing atmosphere of 100% $O_2$ or the like may be used.

The calcined product is pulverized wet (using water as a dispersant) in a ball mill for 30 minutes.

The pulverized product is molded by press work into solid cylindrical pellets, 3 mm in diameter and 3 mm in height, each having embedded therein a pair of Pt-Rh alloy electrodes having a diameter of 100$\mu$. The pellets are baked in air to obtain gas sensitive members. The pellets are baked at 1000° to 2000° C. for 4 hours. The baking temperature is at least 100° C. higher than the calcining temperature. The baking step grows the crystals of $BaSnO_3$ giving the gas sensitive member durability against a high-temperature atmosphere (usually up to 950° C.) during use. This step also sinters the gas sensitive member of $BaSnO_3$ to give enhanced mechanical strength. The baking atmosphere needs only to be non-reducing. For example, an inert atmosphere of 100% $N_2$ or 100% $CO_2$, or a highly oxidizing atmosphere of 100% $O_2$ is usable. With the specimen calcined at 500° C., $BaCO_3$ reacts with $SnO_2$ during the baking step to produce $BaSnO_3$.

The significance of the foregoing steps will be described. The baking step promotes the growth of crystals of $BaSnO_3$, affording resistance to heat during use, especially to reducing atmospheres of high temperatures. The temperature at which $BaSnO_3$ is formed is about 800° C., while the baking temperature is much higher than this temperature. Accordingly the effect of baking is not influenced by the starting materials but is dependent on the baking temperature and time. The baking temperature should be at least 1000° C. and not higher than 2000° C. and is preferably between 1200° C. and 1800° C., more preferably 1260° C. to 1800° C. The highest temperature at which exhaust gas sensors are used appears to be about 950° C., so that the pellet should be baked at least at 1000° C., preferably at least 1200° C. The specimen baked at 1000° C. is about 20 m$^2$/g in specific surface area and about 0.04$\mu$ in mean crystallite size. Baking at 1200° C. results in a specific surface area of about 2.5 m$^2$/g and a mean crystallite size of 0.3$\mu$. The sensitivity of $BaSnO_3$ to oxygen remarkably increases when the baking temperature is at least 1260° C. It is therefore preferable that $BaSnO_3$ be up to 1.5 m$^2$/g in specific surface area and at least 0.5$\mu$ in mean crystallite size. The upper limit of the baking temperature is dependent on the difficulty in obtaining higher baking temperatures and also on the reduction of responsiveness to a change of atmosphere due to the compacting of the sensitive member. In view of these, the upper limit to the baking temperature should be 2000° C. (50$\mu$ in mean crystallite size of $BaSnO_3$), preferably 1800° C. (20$\mu$ in mean crystallite size of $BaSnO_3$ and 0.04 m$^2$/g in specific surface area thereof). The baking time is of secondary significance. It is preferably 30 minutes to 20 hours, more preferably 1 to 10 hours, from the viewpoint of ease of process control.

The calcining step, which is of no substantial significance, is intended to preform $BaSnO_3$ and to reduce the shrinkage that would result from baking to give enhanced strength to the gas sensitive member obtained on baking.

The gas sensitive members prepared in the present example were 15 to 40% in porosity. The electrodes may be connected to the sensitive member after baking.

Figure 2:
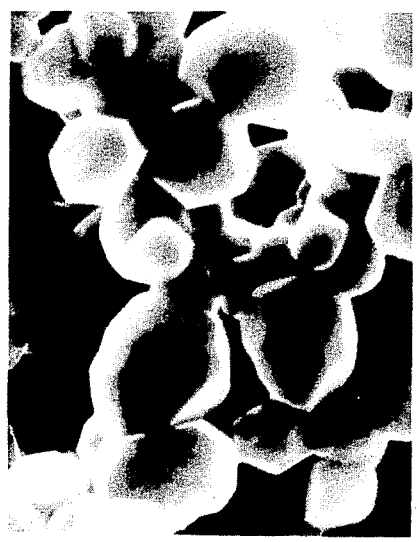
FIG. 2 is an electron photomicrograph of $BaSnO_{3-\delta}$.
Figure 3:
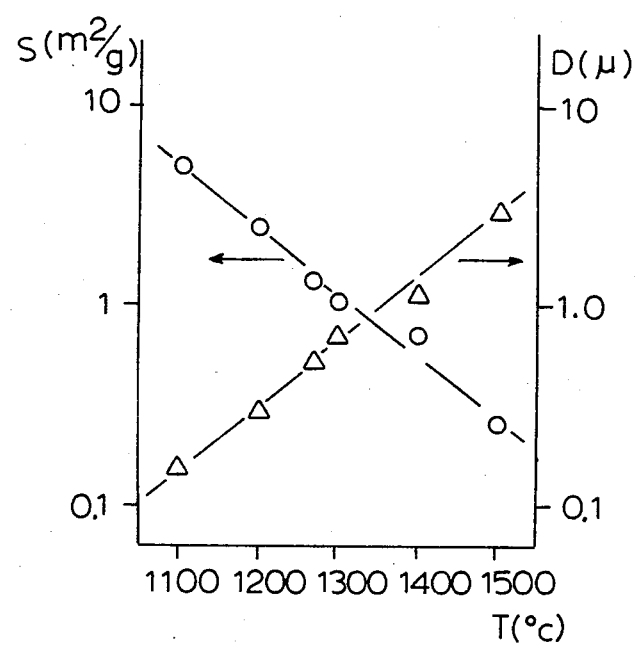
FIG. 3 is a characteristics diagram showing the relation of the baking temperature of $BaSnO_{3-\delta}$ with its mean crystallite size, as well as with its specific surface area.

FIG. 1 is an X-ray diffraction diagram of the specimen (No. A42) obtained at a calcining temperature of 800° C. and baking temperature of 1400° C. The peaks of the diffraction diagram correspond to $BaSnO_3$, and there are no peaks corresponding to unreaced $BaO$, $BaCO_3$ or $SnO_2$. This compound, $BaSnO_3$, is presumed to be a perovskite compound. FIG. 2 is an electron photomicrograph showing the same specimen (No. A42) at 10000X. FIG. 3 shows the relation of the baking temperature with the specific surface area, as well as with the mean crystallite size, as determined with the specimens calcined at 800° C.

(B) Preparation of other materials

Similarly, $SrCO_3$, $CaCO_3$ or $RaCO_3$ is mixed with $SnO_2$ in an equimolar ratio, and the mixture is treated in the same manner as for the preparation of $BaSnO_3$ to obtain perovskite compounds $SrSnO_3$, $CaSnO_3$ and $RaSnO_3$. Furthermore, a mixture of $BaCO_3$ and $SrCO_3$ is reacted with $SnO_2$ to obtain compounds such as $Ba_{0.9}Sr_{0.1}SnO_3$.

Table 1 shows the specific surface areas and mean crystallite sizes of these compounds which are calcined at 800° C.

TABLE 1

| No. | Composition | Baking temperature (°C.) | Specific surface area (m²/g) | Mean crystallite size (μ) |
|---|---|---|---|---|
| 11 | $BaSnO_3$ | 1000 | 20 | 0.04 |
| 12 | " | 1100 | 5.0 | 0.15 |
| 13 | " | 1200 | 2.5 | 0.3 |
| 14 | " | 1230 | 2.0 | 0.4 |
| 15 | " | 1270 | 1.4 | 0.55 |
| 16 | " | 1300 | 1.1 | 0.7 |
| 17 | " | 1400 | 0.5 | 1.2 |
| 18 | " | 1500 | 0.25 | 2.9 |
| 21 | $RaSnO_3$ | 1400 | 0.4 | 2 |
| 31 | $SrSnO_3$ | 1000 | 16 | 0.05 |
| 32 | " | 1100 | 4.0 | 0.2 |
| 33 | " | 1200 | 2.1 | 0.4 |
| 34 | $SrSnO_3$ | 1300 | 1.0 | 0.7 |
| 35 | " | 1400 | 0.4 | 2.0 |
| 36 | " | 1500 | 0.2 | 4.0 |
| 41 | $CaSnO_3$ | 1000 | 3.0 | 0.25 |
| 42 | " | 1100 | 1.2 | 0.6 |
| 43 | " | 1200 | 0.6 | 1.3 |
| 44 | " | 1300 | 0.3 | 2.5 |
| 45 | " | 1400 | 0.2 | 3.5 |
| 46 | " | 1500 | 0.1 | 8 |
| 51 | $Ba_{0.9}Sr_{0.1}SnO_3$ | 1400 | 0.5 | 1.2 |
| 52 | $Ba_{0.5}Sr_{0.5}SnO_3$ | 1400 | 0.5 | 1.3 |
| 53 | $Ba_{0.1}Sr_{0.9}SnO_3$ | 1400 | 0.4 | 2.0 |

(C) Supplement

Table 1 reveals that the specific surface area is in inverse proportion to the mean crystallite size and does not vary independently thereof. Accordingly, the mean crystallite size will be used for indicating the degree of growth of crystals. The mean crystallite size is thus used as a parameter of the growth of crystals because it is difficult to measure the specific surface area, especially because it is very difficult to measure the specific surface area of $ASnO_3$ only when $ASnO_3$ is used as mixed with other substance.

Our experiments have shown that the calcining temperature produces little or no influence on the properties of gas sensitive members, so that the results given below are those achieved by the specimens which were calcined at 800° C.

(D) Comparative examples

The same $SnO_2$ as used for preparing $ASnO_3$ was singly calcined at 800° C. for 1 hour, pulverized and then heated at 1400° C. in air for 4 hours to prepare a comparative specimen in the same manner as above.

Furthermore, $MgO$ or $MgCO_3$ was admixed with $SnO_2$ in an equimolar ratio, and the mixture was calcined in air at 500° to 1200° C. for 1 hour. However, no $MgSnO_3$ was produced, but the product obtained was a mixture of $MgO$ or $MgCO_3$, $SnO_2$ and $Mg_2SnO_4$. To clarify the effect of addition of Mg, a mixture of 90 mol % of $SnO_2$ and 10 mol % of $MgO$ was tested, but the product obtained had properties similar to those of the specimen prepared from $SnO_2$ alone.

Structure of exhaust gas sensor

Figure 4B:
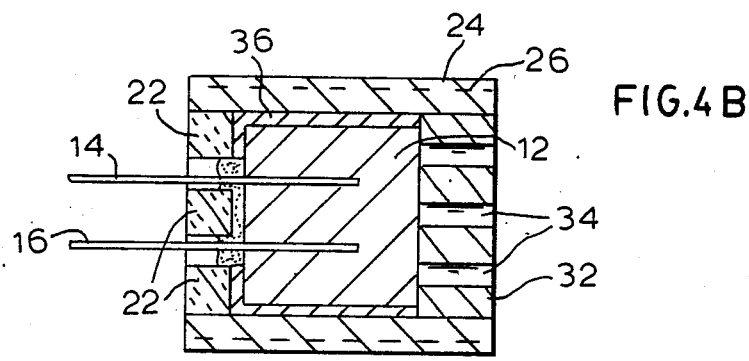
FIG. 4 (A) is a view in longitudinal section of an exhaust gas sensor.
Figure 4A:
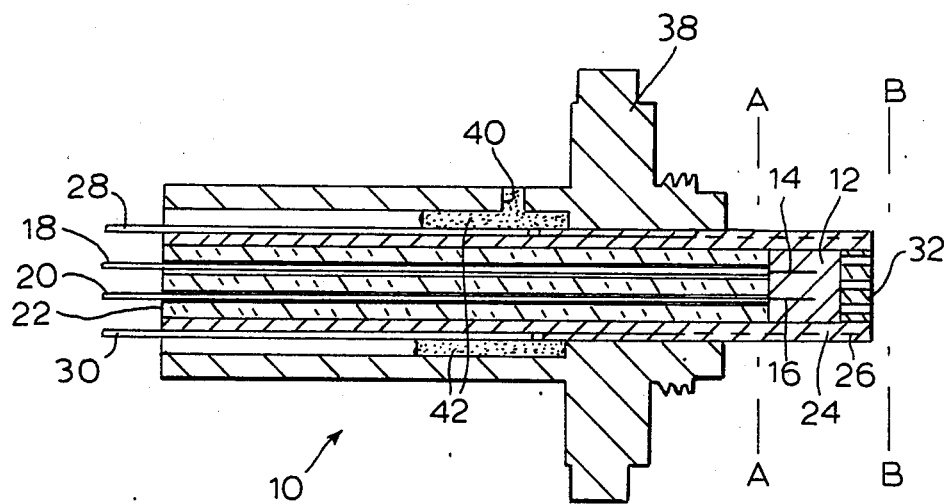

With reference to FIGS. 4 (A) and (B), the structure of an exhaust gas sensor 10 will be described. Indicated at 12 is the above-mentioned gas sensitive member which is in the form of a solid cylindrical pellet. A pair of Pt-Rh alloy electrodes 14 and 16 are implanted in the member 12. Since the electrodes 14 and 16 are expensive, base metal lead wires 18 and 20 of Fe-Cr-Al alloy are connected to the outer ends of the electrodes for access to the internal resistance of the sensitive member 12.

Indicated at 22 is a heat-resistant insulating substrate made of alumina and in the form of a tube having two bores. The exposed ends of the electrodes 14, 16 and the lead wires 18, 20 are accommodated in the bores of the substrate 22 and are mechanically supported by the substrate 22, which also protects the electrodes 14, 16 and the like from corrosion due to the exhaust gas. The bottom of the sensitive member 12 is supported by the substrate 22. While heat-resistant insulating materials are useful for the substrate 22, alumina is used for the present embodiment to assure resistance to thermal impact.

A heater tube 24 is fitted around and bonded to the substrate 22 with use of an unillustrated inorganic adhesive or the like. The gas sensitive member 12 is accommodated in a cylindrical cavity defined by the heater tube 24 and the substrate 22 and is thereby protected from a high-speed exhaust gas stream or the like. The member 12 is suitably heated by the heater tube 24, which comprises a heat-resistant insulating tube, for example, of alumina having embedded in its wall an electrically conductive pattern 26 of tungsten, tin oxide, platinum, ruthenium or the like. The conductive pattern 26, serving as a heat generator for the heater tube 24, is disposed concentrically around the gas sensitive member 12 and connected to heater lead wires 28, 30 toward the base portion of the heater tube 24. The heater tube 24 is characterized in that the conductive pattern 26 is embedded in the tube 24, whereby the conductive pattern 26 is protected from corrosion due to the exhaust gas and mechanical damage. The heater tube 24 is prepared, for example, by printing a conductive pattern 26 of tungsten or the like on the outer peripheral surface, for example, of an alumina tube, coating the pattern with alumina to a thickness of about 100 μ and sintering the coating to form a compact protective coating layer.

The heater tube 24 is controlled, for example, by the method disclosed in U.S. Pat. No. 3,946,198 to maintain the gas sensitive member 12, for example, at a temperature of about 700° C.

The heater tube 24 has an exhaust gas inlet which is provided with a honeycomb 32. As an example of oxidizing catalyst layer, the honeycomb 32 has an oxidizing catalyst supported thereon. The honeycomb 32 serves to mechanically protect the gas sensitive member 12 and to remove combustible components from the exhaust gas. The honeycomb 32 of the present embodiment is 1.2 mm in thickness and has numerous pores 34 having a diameter of 150μ. An oxidizing catalyst of precious metal, such as Pt, Pd or Rh, is supported on the walls defining the pores 34. A spinel compound $MgAl_2O_4$ is used for forming the honeycomb 32. While the exhaust gas passes through the pores 34 of the honeycomb 32, the unreacted combustible components therein react with oxygen, with the result that the composition of the exhaust gas approaches a chemical equilibrium. The oxidizing activity of the honeycomb 32 diminishes the detection error of the gas sensitive member 12 due to its sensitivity to the combustible components. The honeycomb 32 may be replaced by other oxidizing catalyst layer which comprises, for example, Pt supported on $\gamma$-$Al_2O_3$. The intermediate layer 36 to be described below may have a precious metal or like oxidizing catalyst supported thereon to serve as an oxidizing catalyst layer. In this case, however, the gas sensitive member 12 may preferably be provided with a cover for protection from the exhaust gas stream. Such an oxidizing catalyst layer can be dispensed with.

Incidentally, $ASnO_3$ has the property of reacting with alumina at a temperature of not lower than 1200° C. and decposing into $AAl_2O_4$ and $SnO_2$. Accordingly, the gas sensitive member 12 is separated from alumina and thereby protected against reaction with alumina. According to the present embodiment, an intermediate layer 36 made of a spinel compound $MgAl_2O_4$ and having a suitable thickness, for example, of 100μ is provided between the gas sensitive member 12, and the substrate 22 and heater tube 24. The spinel compound $MgAl_2O_4$ is more stable than alumina, and the aluminum in spinel does not react with $BaSnO_3$ or the like. Further, magnesium has low reactivity with tin as already mentioned. Materials which do not react with the gas sensitive member 12 are useful for forming the intermediate layer 36. Besides $MgAl_2O_4$, preferable materials are mullite $Al_6Si_2O_{13}$ and cordierite $Mg_2Al_4Si_5O_{18}$. The intermediate layer 36 is not shown in FIG. 4 (A).

For attaching the sensor 10 to an exhaust pipe or the like, the heater tube 24 is provided with a mount 38. Through a small hole 40 in the mount 38, an inorganic adhesive 42 is filled into the interior space of the mount around the heater tube 24 to bond the mount 38 to the tube 24.

Durability

The problem of durability arises when exhaust gas sensors are used in a reducing atmosphere of high temperature. Specimens were subjected for 10 hours to repeated cycles each comprising 3 seconds in an atmosphere of $\lambda=0.8$ and 1 second in an atmosphere of $\lambda=0.9$. The combustion gas used was a mixture of CO and air. CO, which is most amenable to complete combustion, was used as a fuel to minimize the amount of unreacted component in the exhaust gas. Each specimen was heated at 900° C. The cycle simulates the exhaust gas from motor vehicle engines during high acceleration.

Table 2 shows the changes in resistance value resulting from the test, in the lean region ($\lambda=1.1$) and the rich region ($\lambda=0.9$). It is seen that $ASnO_3$ compounds have high durability and that sufficient durability is available when the baking temperature is at least 1100° C.

TABLE 2

| No. | Result at $\lambda = 1.1$[*1] | Result at $\lambda = 0.9$[*1] |
|---|---|---|
| 11 | 0.9 | 0.9 |
| 12 | 1.0 | 1.0 |
| 13 | No change | No change |
| 16 | " | " |
| 17 | " | " |
| 18 | " | " |
| 21 | " | " |
| 31 | 0.9 | 0.9 |
| 32 | 1.0 | 1.0 |
| 35 | No change | No change |
| 41 | 0.9 | 0.95 |
| 42 | 1.0 | 1.0 |
| 45 | No change | No change |
| $SnO_2$[*2] | 0.03 | 0.3 |

[*1] Ratio of resistance value after test to resistance value before test.
[*2] Comparative example.

Sensitivity to combustible gas

Preferably, the sensitivity to combustible gases is small. Usual metallic oxide semiconductors are exceedingly more sensitive to combustible gases than to oxygen, such that in the region of $\lambda>1$, the resistance value is governed by the concentration of unreacted combustible gas and does not accurately reflect $\lambda$. Accordingly, $\lambda$ can be detected accurately when the sensitivity to the combustible gas is suppressed to the same level as the sensitivity to oxygen.

For testing, specimens were maintained at 700° C. and brought into contact with an exhaust gas having a $\lambda$ value of 1.1. One mole % of $CH_4$ and 2.2 mole % of $O_2$ per 100 mole % of the exhaust gas were introduced into the flow of exhaust gas immediately upstream from the specimen to check the effect of unreacted $CH_4$. Table 3 shows the change in the resistance value due to the introduction of $CH_4$. The result is given in terms of the ratio of resistance value after the introduction of $CH_4$ to the resistance value before the introduction of $CH_4$.

The combustible gas sensitivity is influenced by the size of the gas sensitive member 12; the sensitivity increases as the size of the member 12 diminishes. For example, if the gas sensitive member 12 is about 0.5 mm in diameter and height, the value of Result 1 achieved by specimen 17 in Table 3 becomes 0.85 to 0.9. This appears attributable to the fact that while the unreacted combustible gas diffuses through the sensitive member 12 of large size, the gas reacts with oxygen and is thereby removed owing to the oxidizing activity of $ASnO_3$.

TABLE 3

| No. | Result 1[*1] | Result 2[*2] |
|---|---|---|
| 11 | 0.96 | 0.99 |
| 12 | 0.98 | 1.0 |
| 13 | 1.0 | " |
| 16 | No change | " |
| 17 | " | " |
| 18 | " | " |
| 21 | 1.0 | 1.0 |
| 45 | 1.0 | " |

TABLE 3-continued

| No. | Result 1*[1] | Result 2*[2] |
|---|---|---|
| SnO$_2$*[3] | 0.03 | 0.5 |

*[1]With the honeycomb 32 removed.
*[2]With the honeycomb 32 attached.
*[3]Comparative example.

Characteristics around $\lambda=1$

Figure 5:
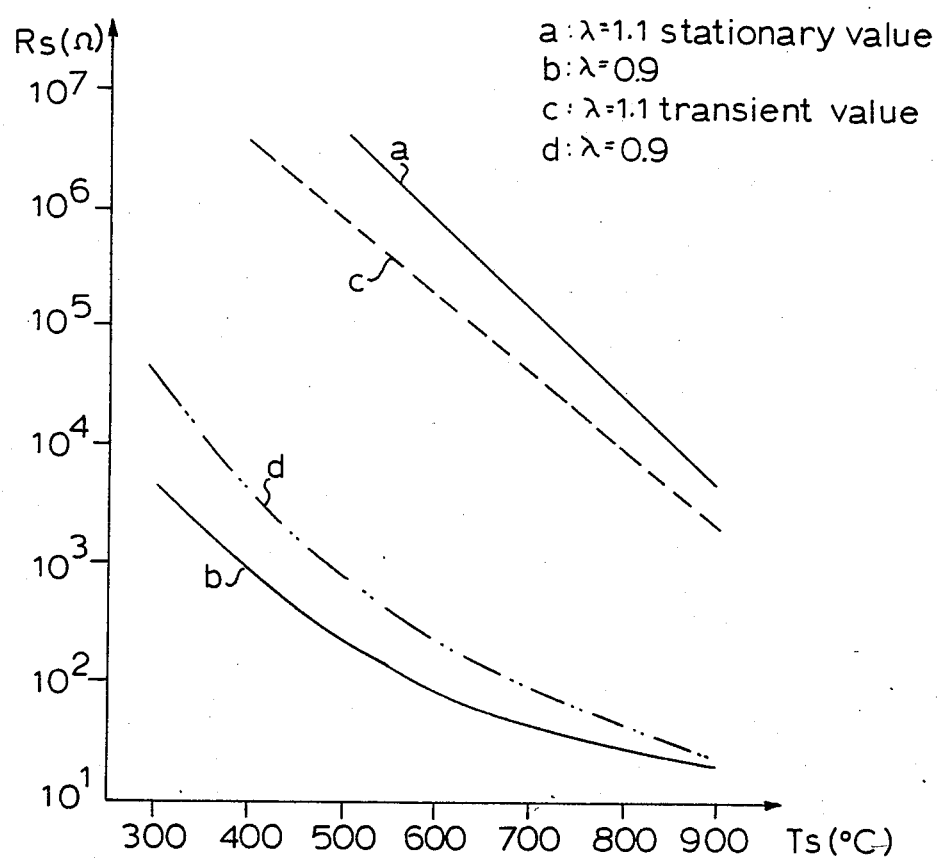
FIG. 5 is a characteristics diagram of $BaSnO_{3-\delta}$.

Specimens were checked for the stationary value of resistance at $\lambda=1.1$ and $\lambda=0.9$. Next, each specimen was exposed to atmospheres of $\lambda=1.1$ and $\lambda=0.9$, for 1 second to each, and checked for the transient value of resistance. The result achieved by specimen 17 is shown in FIG. 5, the result of specimen 35 in FIG. 6, and the result of specimen 45 in FIG. 7. Specimen 21 is similar to specimen 17 in characteristics.

These diagrams show the sensitivity, resistance, temperature coefficient of resistance and responsiveness of the specimens in the event of change from $\lambda>1$ to $\lambda<1$. A comparison of the diagrams reveals that BaSnO$_3$ and RaSnO$_3$ are distinctly characterized by n-type properties with a great change in resistance value between $\lambda>1$ and $\lambda<1$ and that SrSnO$_3$ and CaSnO$_3$ are less distinct in n-type properties and undergo a smaller change in resistance between $\lambda>1$ and $\lambda<1$. Further CaSnO$_3$ is of less n-type properties than SrSnO$_3$.

Figure 6:
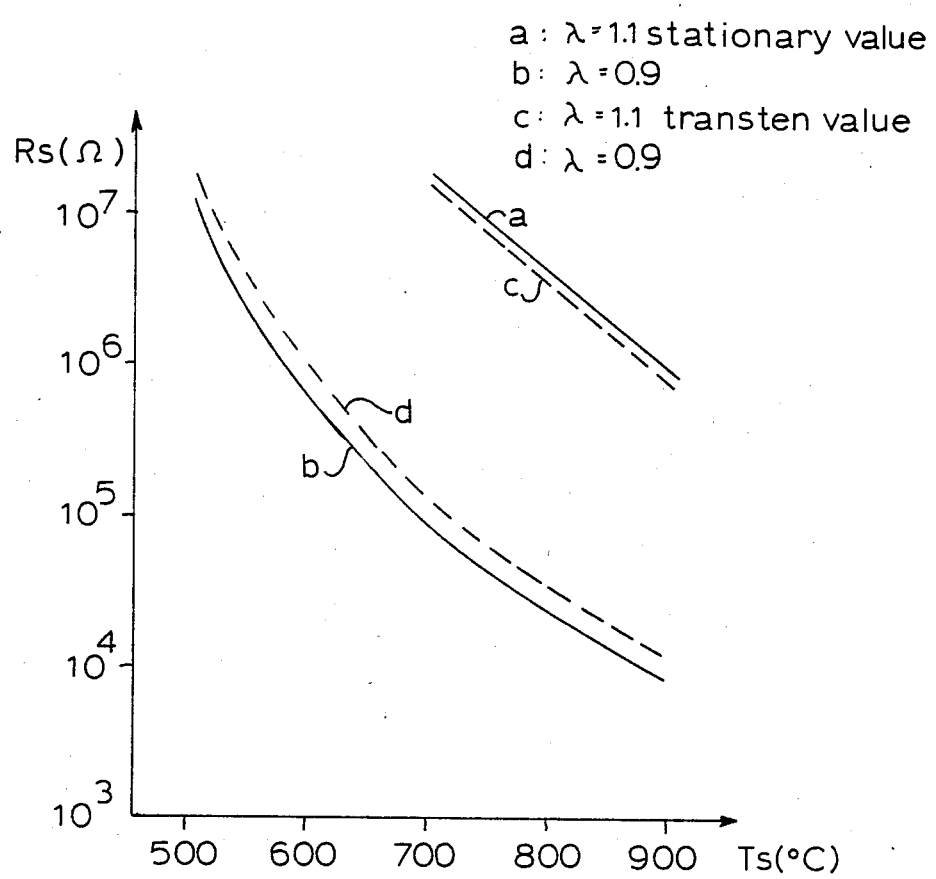
FIG. 6 is a characteristics diagram of $SrSnO_{3-\delta}$.
Figure 7:
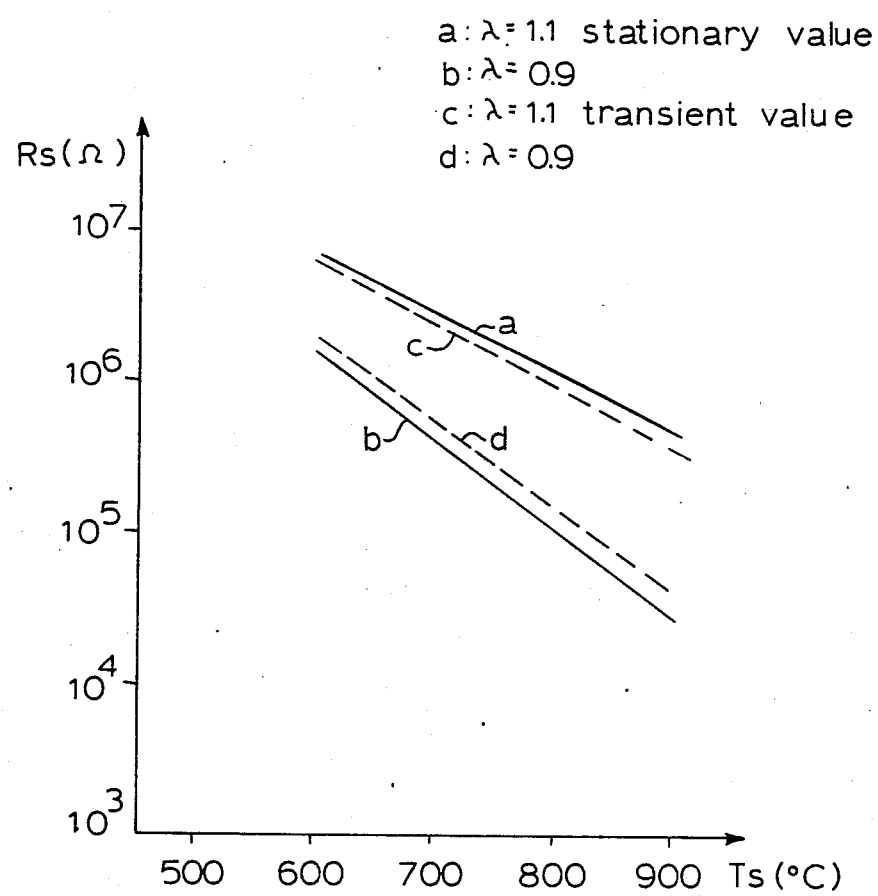
FIG. 7 is a characteristics diagram of $CaSnO_{3-\delta}$.

The response speed will be expressed in terms of log (Rc/Rd)/log (Ra/Rb) wherein Rc is a transient resistance value at $\lambda=1.1$, Rb is a stationary value at $\lambda=0.9$, Ra is a stationary value at $\lambda=1.1$, and Rd is a transient value at $\lambda=0.9$. In FIGS. 5 to 7, the value of the above expression corresponds to the spacing between the transient values divided by the spacing between the stationary values. Table 4 shows the values of chief specimens at 700° C. Each specimen of the invention is higher in response speed than SnO$_2$ of the comparative example.

TABLE 4

| No. | log(Rc/Rd)/log (Ra/Rb) |
|---|---|
| 11 | 0.72 |
| 12 | 0.75 |
| 17 | 0.76 |
| 21 | 0.84 |
| 31 | 0.86 |
| 35 | 0.92 |
| 41 | 0.78 |
| 45 | 0.80 |
| SnO$_2$* | 0.44 |

*Comparative example

Oxygen sensitivity

Figure 8:
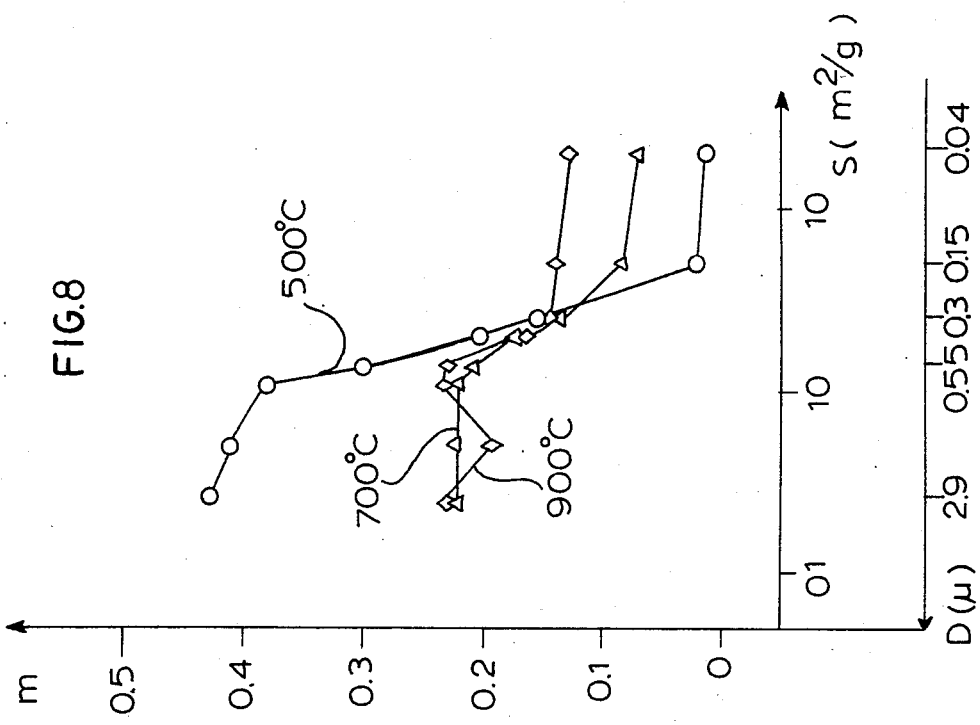
FIG. 8 is a characteristics diagram of $BaSnO_{3-\delta}$ showing the relation of the specific surface area, as well as of the mean crystallite size, with the oxygen sensitivity.
Figure 9:
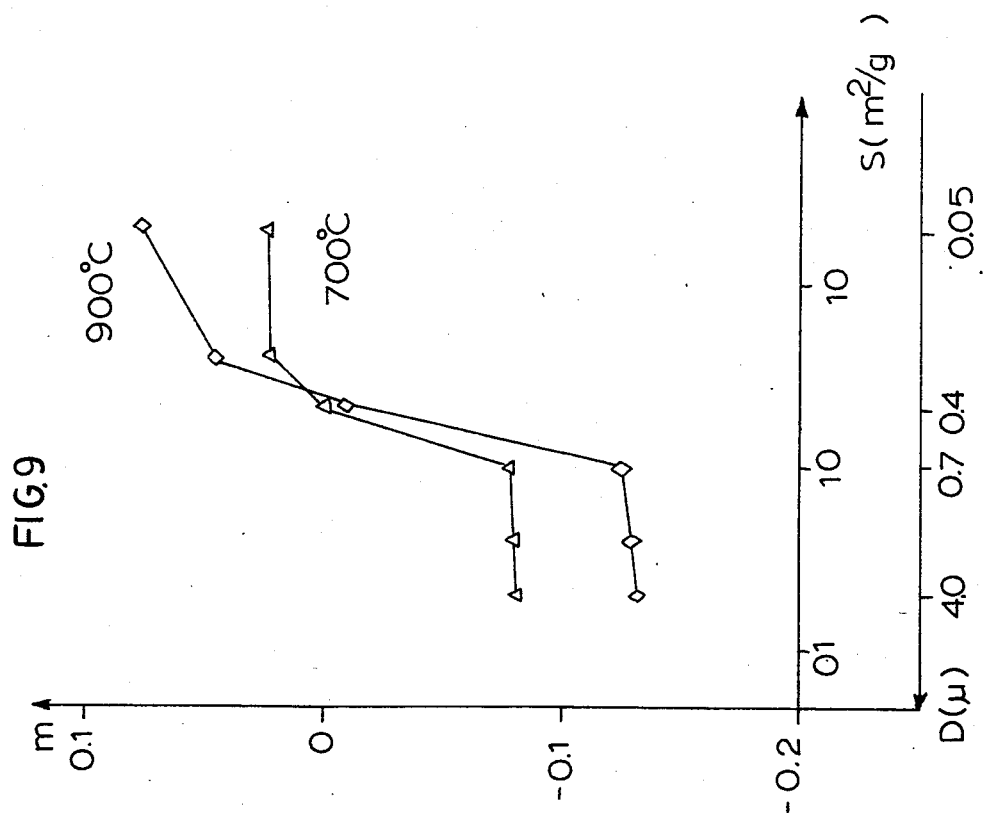
FIG. 9 is a characteristics diagram of $SrSnO_{3-\delta}$ showing the relation of the specific surface area, as well as of the mean crystallite size, with the oxygen sensitivity.
Figure 10:
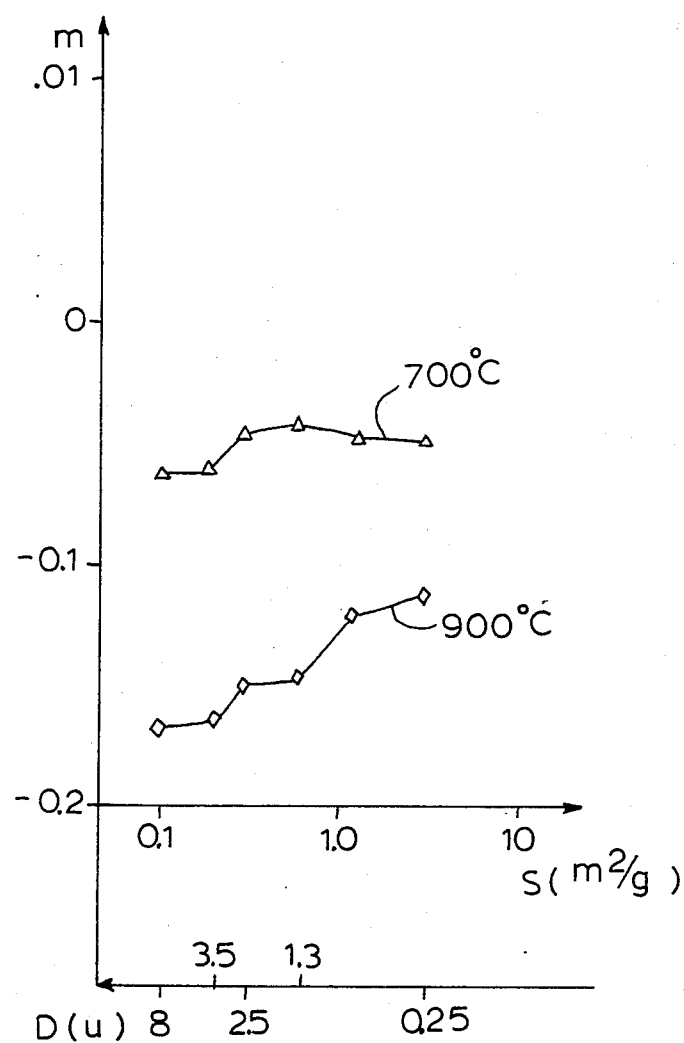
FIG. 10 is a characteristics diagram of $CaSnO_{3-\delta}$ showing the relation of the specific surface area, as well as of the mean crystallite size, with the oxygen sensitivity.

BaSnO$_3$, SrSnO$_3$ and CaSnO$_3$ were tested at varying oxygen partial pressures under N$_2$ balance to determine the relation of the oxygen sensitivity with the specific surface area S, as well as with the mean crystallite size D. The results are shown in FIGS. 8 to 10, in which m plotted as ordinate represents oxygen gradient. The results achieved by BaSnO$_3$ are given in FIG. 8, those by SrSnO$_3$ in FIG. 9, and those by CaSnO$_3$ in FIG. 10. Specimen 21 is close to specimen 17 in m value.

These diagrams indicate that the oxygen sensitivity increases as the growth of crystals is promoted (to decrease S). It is seen that in the case of BaSnO$_3$, m increases remarkably when the specific surface area is less than 1.5 m$^2$/g. Another feature is that whereas m is positive for BaSnO$_3$, m is negative for SrSnO$_3$ when S is less than 1 m$^2$/g and is negative for CaSnO$_3$ at all times.

SrSnO$_3$ and CaSnO$_3$ wherein the growth of crystals is promoted exhibit p-type properties in the lean burn region.

Incidentally, FIGS. 8 to 10 show oxygen sensitivities as static characteristics. The oxygen sensitivity, when measured in a dynamic mode, is lower by an amount corresponding to a deficiency in responsiveness to a change in oxygen partial pressure.

Inherently, BaSnO$_3$ is similar to RaSnO$_3$, and SrSnO$_3$ to CaSnO$_3$. In properties, Ba$_{1-x}$Ra$_x$SnO$_3$ is similar to BaSnO$_3$, and Ca$_{1-x}$Sr$_x$SnO$_3$ to CaSnO$_3$ or SrSnO$_3$. Table 5 shows the oxygen gradient of Ba$_{1-x}$Sr$_x$SnO$_3$. It is seen that with respect to the oxygen gradient, the compound is intermediate between BaSnO$_3$ and SrSnO$_3$ according to the value of x.

TABLE 5

| No. | Composition | m (900° C.) | m (700° C.) |
|---|---|---|---|
| 17 | BaSnO$_3$ | 0.19 | 0.22 |
| 51 | Ba$_{0.9}$Sr$_{0.1}$SnO$_3$ | 0.17 | 0.20 |
| 52 | Ba$_{0.5}$Sr$_{0.5}$SnO$_3$ | 0.03 | 0.02 |
| 53 | Ba$_{0.1}$Sr$_{0.9}$SnO$_3$ | −0.14 | −0.05 |
| 35 | SrSnO$_3$ | −0.13 | −0.08 |

Output in lean burn region

Figure 11:
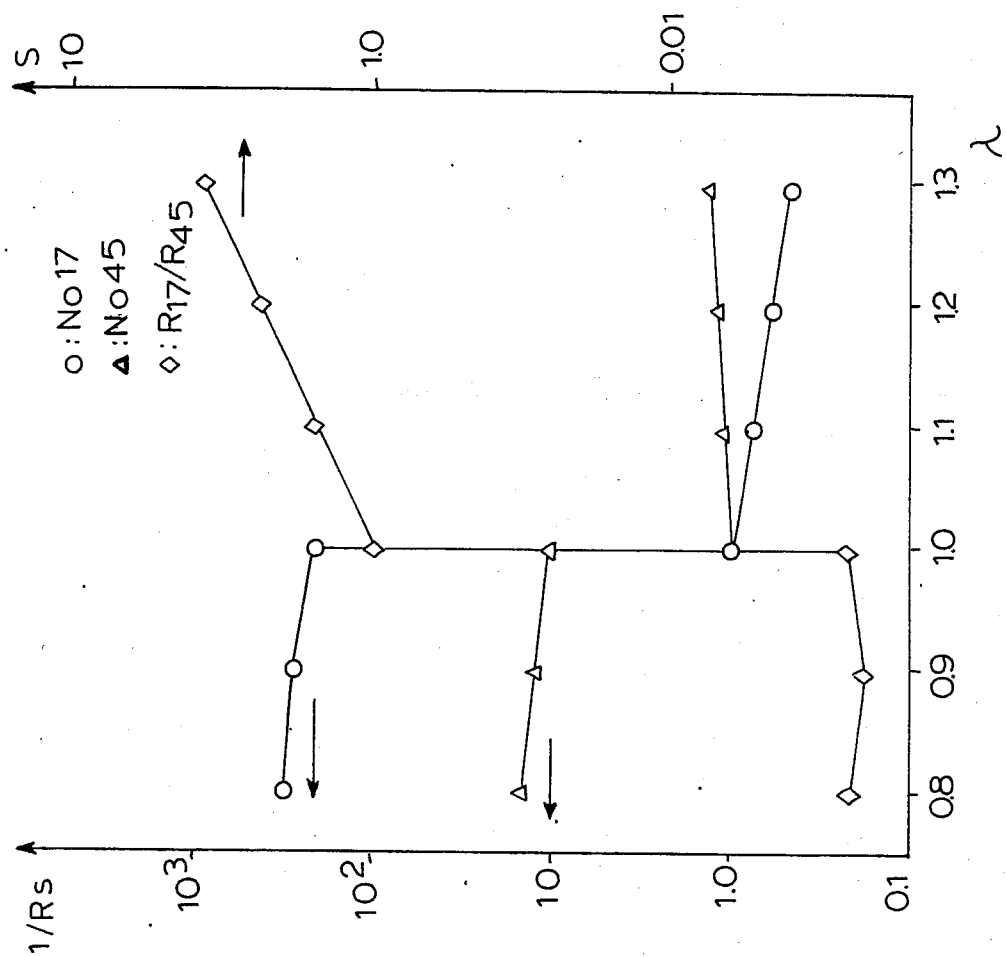
FIG. 11 is a characteristics diagram of $BaSnO_{3-\delta}$ and $CaSnO_{3-\delta}$ showing the relation between the resistance and the air/fuel ratio.

As gas sensitive members 12, specimens 17 and 45 were tested as heated at 900° C., with the results shown in FIG. 11. Plotted as the left-side ordinate is the reciprocal of resistance value (based on the value at $\lambda=1.0+\delta$). Plotted as the right-side ordinate is the ratio S of specimen 17 to specimen 45 in resistance value (1 at $\lambda=1.0+\delta$).

With increasing air/fuel ratio $\lambda$, the resistance value of CaSnO$_3$ (specimen 45) increases once at the point of equivalence and thereafter decreases in the lean burn region, whereas the resistance value of BaSnO$_3$ (specimen 17) increases with the air/fuel ratio.

Supplement

The compounds ASnO$_3$ described above can be used as admixed with other substances. Any substance may be added to ASnO$_3$ insofar as the characteristics of the gas sensitive member 12 are governed by ASnO$_3$. The compound ASnO$_3$ may be used as admixed, for example, with SnO$_2$. Since the characteristics of perovskite compounds are insensitive to the replacement of their component elements as already known (e.g. U.S. Pat. No. 3,558,280), the element A and Sn element of the compound ASnO$_3$ may be replaced by other metal elements, each in a proportion of up to 20 mole %, preferably up to 10 mole %, more preferably up to 3 mole %. Because the characteristics of the compound ASnO$_3$ are not sensitive to replacement, replacement of up to 3 mole % is not very effective. The replacement is effective chiefly for varying the resistance value and the temperature coefficient of resistance. Replacement of up to 10 mole % is slightly less effective; up to 20 mole % of other element can be substituted. Examples of useful substituent elements for A are Mg, lanthanides with atomic numbers of 57 to 71 and actinides with atomic numbers of 89 to 103. Sn can be replaced, for example, by transition metals, Ga, In, Tl, Ge, Pb, Sb, and Bi.

What is claimed is:

1. An exhaust gas sensor including a gas sensitive member comprising a metallic oxide semiconductor capable of undergoing variations in resistance, and at least one pair of electrodes connected to the gas sensitive member, the exhaust gas sensor being characterized in that the metallic oxide semiconductor is a compound $ASnO_{3-\delta}$ wherein A is at least one element selected from the group consisting of Ba, Sr, Ca and Ra, and $\delta$ is a non-stoichiometric parameter.

2. An exhaust gas sensor as defined in claim 1 wherein the element A is Ba.

3. An exhaust gas sensor as defined in claim 1 wherein the compound $ASnO_{3-\delta}$ is 0.04 to 20$\mu$ (microns) in mean crystallite size.

4. An exhaust gas sensor as defined in claim 3 wherein the element A is Ba, and the compound $BaSnO_{3-\delta}$ is 0.3 to 20$\mu$ (microns) in mean crystallite size.

5. An exhaust gas sensor as defined in claim 4 wherein the compound $BaSnO_{3-\delta}$ is 0.5 to 20$\mu$ (microns) in mean crystallite size.

6. An exhaust gas sensor as defined in claim 5 wherein the compound $BaSnO_{3-67}$ is 1.5 to 0.04 m$^2$/gram in specific surface area and 0.5 to 20$\mu$ (microns) in mean crystallite size.

7. An exhaust gas sensor as defined in claim 1 wherein the gas sensitive member is supported by an alumina substrate, and an intermediate layer made of a heat-resistant insulating material is provided between the alumina substrate and the gas sensitive member, the heat-resistant insulating material being not reactive with the compound $ASnO_{3-\delta}$.

8. An exhaust gas sensor as defined in claim 7 wherein the intermediate layer is made of at least one member selected from the group consisting of spinel ($MgAl_2O_4$), mullite ($Al_6Si_2O_{13}$) and cordierite ($Mg_2Al_4Si_5O_{18}$).

9. A process for producing an exhaust gas sensor comprising a gas sensitive member and at least one pair of electrodes connected to the sensitive member, the process being characterized in that at least one substance selected from the group consisting of compounds $ASnO_{3-\delta}$ (wherein A is at least one element selected from the group consisting of Ba, Sr, Ca and Ra, and $\delta$ is a non-stoichiometric parameter) and a substance which is converted to a compound $ASnO_{3-\delta}$ by heating is baked in a non-reducing atmosphere at 1000° to 2000° C. to prepare the gas sensitive member.

10. A process as defined in claim 9 wherein the baking temperature is 1260° to 1800° C.

11. A process as defined in claim 10 wherein the element A is Ba.

12. a process as defined in claim 9 wherein the baking time is 30 minutes to 20 hours.

13. A process as defined in claim 10 wherein the baking time is 1 to 10 hours.

* * * * *